(12) United States Patent
Fischell

(10) Patent No.: US 10,736,792 B1
(45) Date of Patent: Aug. 11, 2020

(54) MEANS AND METHOD TO STOP BLEEDING FROM THE NOSE

(71) Applicant: Robert E. Fischell, Dayton, MD (US)

(72) Inventor: Robert E. Fischell, Dayton, MD (US)

( * ) Notice: Subject to any disclaimer, the term of this patent is extended or adjusted under 35 U.S.C. 154(b) by 0 days.

(21) Appl. No.: 16/397,062

(22) Filed: Apr. 29, 2019

(51) Int. Cl.
*A61F 13/20* (2006.01)
*A61M 31/00* (2006.01)
*A61F 13/00* (2006.01)
*A61F 13/551* (2006.01)
*A61F 13/38* (2006.01)

(52) U.S. Cl.
CPC .... *A61F 13/2005* (2013.01); *A61F 13/00063* (2013.01); *A61F 13/38* (2013.01); *A61F 13/55175* (2013.01); *A61M 31/00* (2013.01); *A61M 2210/0618* (2013.01)

(58) Field of Classification Search
CPC .................. A61F 13/2005; A61F 13/38; A61F 13/55175; A61F 13/00063; A61F 2013/00476; A61F 13/36; A61M 2210/061; A61M 31/00; A61B 17/24; A61B 2017/246; A61B 17/12104; A61B 2017/12004; A61B 17/12131
See application file for complete search history.

(56) References Cited

U.S. PATENT DOCUMENTS

| | | | | |
|---|---|---|---|---|
| 1,573,648 A | * | 2/1926 | Sheely | B65D 47/42 604/1 |
| 3,074,542 A | * | 1/1963 | Myerson | A61M 5/3202 206/365 |
| 5,084,005 A | * | 1/1992 | Kachigian | A61B 10/02 600/569 |
| 5,391,179 A | * | 2/1995 | Mezzoli | A61B 17/12104 604/1 |
| 5,584,822 A | | 12/1996 | Lively et al. | |
| 5,601,594 A | * | 2/1997 | Best | A61F 5/08 606/196 |
| 5,702,035 A | | 12/1997 | Tsao | |
| 5,713,855 A | * | 2/1998 | Shippert | A61B 17/12022 604/104 |

(Continued)

OTHER PUBLICATIONS

Suhale, Samia. "How to Stop a Nosebleed at Home: 11 Nose Bleeding Treatments." Dec. 13, 2018. https://optimisticgirls.com/how-to-stop-a-nosebleed-at-home/. Accessed Aug. 15, 2019.*

*Primary Examiner* — Adam Marcetich
(74) *Attorney, Agent, or Firm* — Rosenberg, Klein & Lee

(57) ABSTRACT

A blood coagulant assembly having a blood coagulant device adapted to be placed into a nostril of a patient suffering from a nose bleed. The blood coagulant device being initially placed within a blood coagulant device container which has a top section and a bottom section each secured to the other in a releasable manner. The blood coagulant device being mounted in a fixed position within the blood coagulant device container prior to removal of the blood coagulant device for insertion into a patient's nose that is bleeding. The blood coagulant device having a handle lower section and a handle upper section with a through opening passing through both the lower and upper handle sections. A blood coagulant material is secured onto an outer surface of the blood coagulant device to be placed against an inner surface of the nostril of a patient that is experiencing a bleeding nose for the purpose of stopping the nose from bleeding.

18 Claims, 3 Drawing Sheets

(56) References Cited

U.S. PATENT DOCUMENTS

| | | | |
|---|---|---|---|
| 6,386,197 B1* | 5/2002 | Miller | A61F 5/08 |
| | | | 128/200.24 |
| 6,768,040 B1 | 7/2004 | Sessions et al. | |
| 8,932,560 B2 | 1/2015 | Dowling et al. | |
| 9,943,157 B1* | 4/2018 | Chang | A45D 34/042 |
| 2004/0135105 A1* | 7/2004 | Hutcheson | G21F 5/015 |
| | | | 250/506.1 |
| 2005/0149173 A1 | 7/2005 | Hunter et al. | |
| 2012/0046607 A1* | 2/2012 | Syk | A61F 11/08 |
| | | | 604/103.02 |
| 2012/0053567 A1* | 3/2012 | Schreck | A61B 17/24 |
| | | | 604/514 |
| 2013/0116656 A1 | 5/2013 | Song | |
| 2013/0184684 A1* | 7/2013 | Yardley | A61F 13/126 |
| | | | 604/514 |
| 2015/0209191 A1* | 7/2015 | Bruce | A61F 13/2005 |
| | | | 604/2 |
| 2016/0235953 A1* | 8/2016 | Hsu | A61B 17/12104 |
| 2017/0095374 A1* | 4/2017 | Lauer | A61F 17/00 |
| 2017/0224867 A1* | 8/2017 | Datt | A61L 24/0036 |
| 2018/0264241 A1* | 9/2018 | Plance | A61M 31/002 |
| 2018/0289383 A1 | 10/2018 | Fischell | |
| 2018/0369007 A1* | 12/2018 | Beck | A61F 5/0013 |
| 2019/0254961 A1* | 8/2019 | Mechor | A61F 13/2005 |

* cited by examiner

MEANS AND METHOD TO STOP BLEEDING FROM THE NOSE

FIELD OF USE

This invention is in the field of methods and devices for the treatment of a nose that is bleeding including an optimum means for packaging the nose-bleed-stopping device.

BACKGROUND OF THE INVENTION

There are many human patients who suffer severely from a nose that bleeds with bleeding that is difficult to control. That is particularly true for the many patients who are required to take blood thinners to prevent a stroke that can be caused by atrial fibrillations of the heart. In U.S. Pat. 8,932,560, M. B. Dowling et al describe the use of chitosan that is a natural polysaccharide that is modified with hydrophobic moieties that has the capability to prevent blood from clotting. What is needed for patients who suffer from severe bleeding of the nose is a novel means and method to apply chitosan or some other blood clotting composition to the interior surface within that nostril of the nose that is bleeding. One such blood clotting agent is the drug aluminum chloride-6-hydrate 21.3% (the ACH drug) as described in US Pat. No. 5,702,035. The '035 patent describes the drug ACH as being used with a Q-Tip for cuts that men occasionally experience when shaving. It is envisioned that such a drug, when placed into the outer surface of a sponge-like-material, would be effective in stopping nose bleeds.

In US Pat. No. 5,584,822, B. W. Lively, et al describe a cylindrically-shaped tampon-like device coated with zinc oxide for insertion into the nose to stop bleeding. This design does not envision an efficient means for securing the tampon into a container that efficiently contains the tampon, nor does it describe a means to allow excess blood to leave the nose while the tampon is in place, nor does it describe a coating for the tampon that closes the bleed-opening inside the nose and the zinc oxide does not promote healing of that opening where the bleeding occurs.

In US Pat. No. 6,768,040, R. W. Sessions, et al describe a tapered insert that can be placed into the nose to stop bleeding. However, like Lively's '822 patent, the '040 patent does not describe an interior passageway to allow excess blood to leave the nasal cavity, nor is there described an efficient way to contain the nasal insert within a special bottle prior to its insertion into the nostril. Also, the device described in the '040 patent does not describe any coating for the tampon-like insert that stops bleeding and provides a healing effect on the interior surface of the nose.

In US Patent Application No. US 2013/0116656, Yong Song describes a means for stopping nose bleed that does have a central opening for draining of excessive blood, it does not describe any handle for a device inserted into the nose, nor does it describe any coating of the nasal insert or a special container to provide fast and efficient access to get the device for quick placement into the nose. Still further, the Song application does not describe coating the tapered end of the nose bleed stopper with a medication that can both close the bleeding portion inside the nasal cavity and assist in healing that opening.

SUMMARY OF THE INVENTION

The present invention is a means and method for controlling a severely bleeding nose, particularly for patients who are required to use a blood thinner to preclude the possibility of a stroke that can be caused by atrial fibrillation. The present invention consists of a sponge-like material that is formed into the top section of a nasal insert that is slightly tapered to readily slide up into the bleeding nose and a bottom handle that is used for both inserting the bleed stopping device into the nose and removing it a few minutes later when the bleeding has been essentially stopped. The outside tapered surface of the bleed stopping device is coated and impregnated with the chitosan or the ACH material that contacts the inner surface of the nostril where the bleeding is occurring so as to cause the blood to clot to prevent further bleeding. It is also conceived that the ACH drug has a propensity for healing the bleeding opening in the nasal passageway. Therefore, with repeated usage, eventually stopping the recurrence of nose bleeds. The time for the bleeding to stop would typically be only a few minutes because of the ability of the chitosan or the ACH, or some equivalent bleed stopping drug to force a clotting of the blood at that region within the nostril where the bleeding is occurring.

Another novel feature of the blood coagulant device that is the present invention is a comparatively large diameter hole that extends for the entire length of the device which serves two important functions, namely: (1) to allow excess blood within the patient's nostril and nasal cavity to come out, and (2) when that blood flow ceases, it allows the patient to breathe through that hole. Still further, the present invention has a rigid handle material (such as the plastic Lucite) that extends into the sponge-like material, the handle being used for easy insertion of the device into the nose and for removing the device from the nose after the bleeding has been stopped.

Thus, one object of the present invention is to be able to insert a blood coagulant device coated with chitosan or ACH, or any other bleed-stopping drug, into the nostril of a patient's nose that is bleeding to form a blood clot in order to stop the bleeding.

Another object of this invention is to have the main body of the device be formed from a sponge-like material onto which and into which the chitosan or ACH or similar drug is placed.

Still another object of this invention is to form a handle from a rigid plastic that extends into the sponge-like material that is placed into the nose to make that sponge-like material more rigid for nasal insertion, the handle being designed to be held by the patient for both placing the device into the nostril that is bleeding and removing the device from the nose after the bleeding has been stopped.

Still another object of this invention is to have a hole that extends for the entire interior length of the device that allows for the downward outflow of any blood that has flowed above the top of the device and also allows the patient to breathe through the device until it is removed from the patient's nose.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
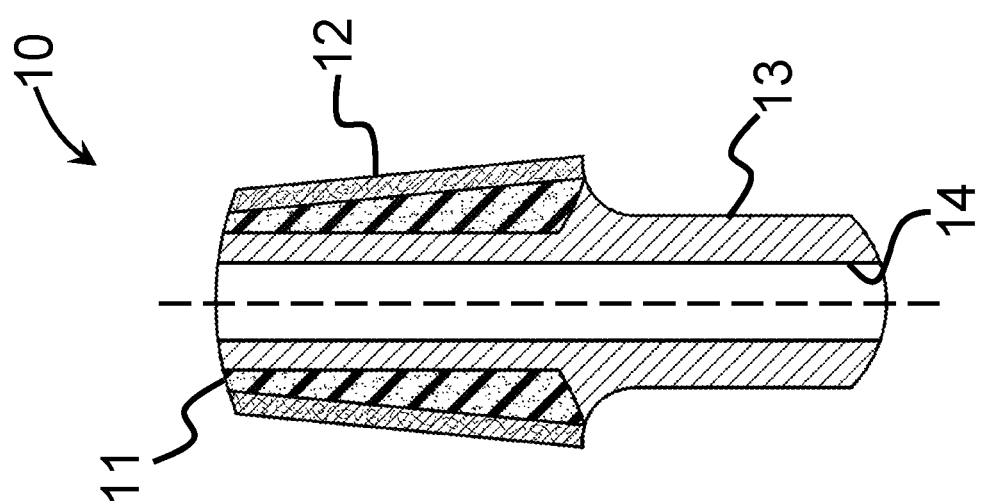
FIG. 1 is a cross-sectional view of the blood clotting device designed for insertion into the nose to stop the bleeding in such a nose.

FIG. 1 is a cross sectional view of the device 10 that is designed for insertion into a patient's nose to stop the bleeding in that nose. The device 10 has a tapered, sponge-like portion 11 that includes a blood clotting drug coating 12 that can stop bleeding in the nose. The drug 12 could be chitosan, aluminum chloride-6-hydrate 21.3% (ACH) or any comparable medication that can stop bleeding from inside a patient's nostril. It is also believed that the drug ACH has that capability to not only stop bleeding, but to heal that portion of the nostril that has been bleeding so that, after extended usage, the patient will encounter fewer and possibly no more nose bleeds. The device 10 has a handle 13 that has a smaller outside diameter within the sponge-like section 11 and extends with a larger outside diameter downward beyond the tapered portion of the device 10. A hole 14 extends through the entire length of the handle 13. One purpose of the hole 14 is to allow for excess blood to come out of the nose when the device 10 is inserted to treat a bleeding nose. The hole 14 also allows for the patient to breathe through that hole 14 at some time after the device 10 has been inserted into that patient's nose and excessive bleeding has stopped.

The bleed-stopping-drug 12 can be an outer coating of the upper portion 11 and it could also be contained for a short distance within the outer region of the sponge-like material 11 from which the upper portion of the device 10 is formed.

To accommodate various sizes of noses that could have bleeding controlled by the device 10, it is expected that the device would come in different lengths and different diameters to accommodate different sizes of a human nostril. The range of sizes would be from as large as 1.0 cm in diameter for the largest diameter of the upper portion 11 to as small as 0.3 cm diameter to accommodate a very small nostril. The length of the upper portion 11 would be approximately 2 cm with a maximum possible length of 4 cm and a minimum possible length of 1.0 cm. The taper of the upper portion 11 could be as little as zero degrees or as much as 10 degrees with an optimum taper being approximately 3 degrees. Although the handle 13 could have a great variety of lengths and diameters, an optimum diameter would be about 2 mm smaller than the diameter at the bottom of the upper portion 11 and the length could be anything from ½ cm to as-long-as 5 cm with an optimum length being approximately 2 cm. The hole 14 that extends through the entire length of the device 10 could have a diameter as small as 1.0 mm to as large as 7 mm with an ideal diameter being approximately 3 mm.

Figure 2:
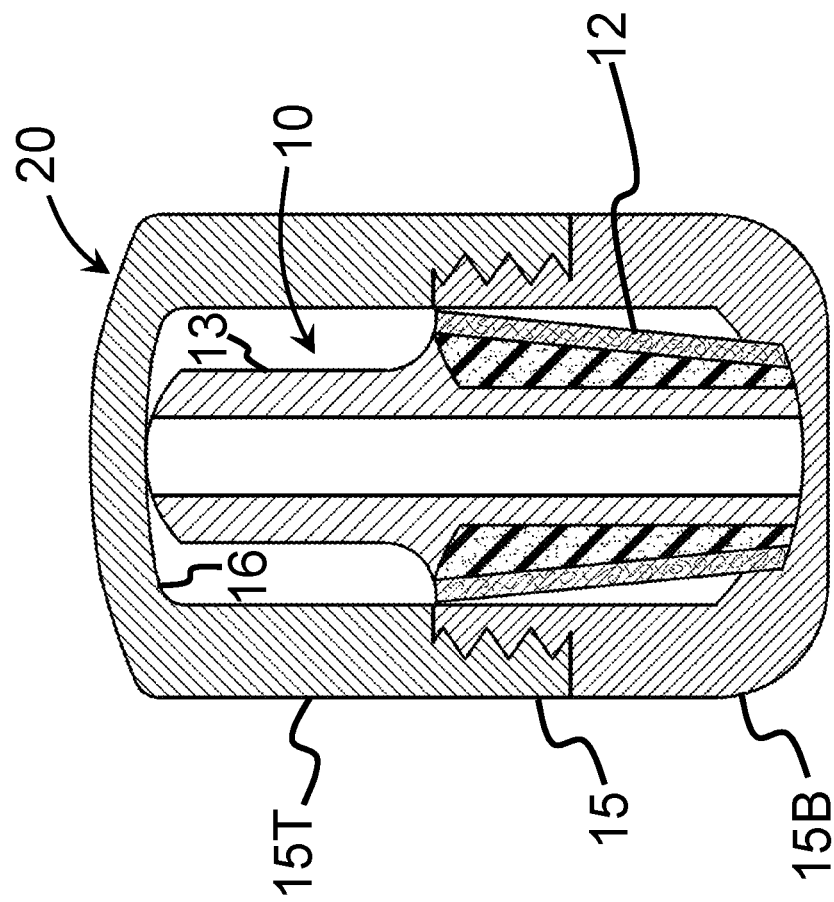
FIG. 2 is a cross section of the blood clotting device for the treatment of a bleeding nose placed inside a specially designed bottle that provides easy access for removing the device from that bottle.

FIG. 2 shows a key feature of the present invention which is the assembly 20, which assembly 20 includes the bottle 15 into which the nose bleed stopping device 10 has been placed. The complete system 20 is to be acquired by patients who have a problem with a bleeding nose. There are two parts of the bottle 15 that are screwed together (or slide-fitted together) to enclose the device 10. The bottle 15 has a bottom section 15B and a top section 15T that are screwed (or slide fitted) together to contain the device 10. The interior of the bottom section 15B is shown to make contact with the coating 12 that has been placed onto and into the sponge-like tapered section 11. Having the interior surfaces of the top and bottom of the bottle 15B in close contact with the top and the bottom of the coating 12 of the tapered section 11, (as shown in FIG. 2) prevents the device 10 from sliding from side-to-side within the bottle 15. The top interior surface 16 inside the top section 15T of the bottle 15 is in close contact with the end of the handle 13 of the device 10. By this design, as shown in FIG. 2, the device 10 remains firmly in place within the bottle 15 prior to its removal for the treatment of a nose bleed.

As soon as a patient realizes that he/she has a nose bleed, the bottle 20 can be accessed and with a simple twist or slide, the top section of the bottle 15 can be removed from the bottom portion 15B. Then, while the device 10 is still within the bottom section 15B of the bottle 15 (that bottom section 15B being held in one of the patient's hands) the other hand can take the nose bleed stopping device 10 by its handle 13 and remove it from the bottom section 15B of the bottle 15. By this means, the device 10 can be readily accessed and immediately placed into that patient's nostril to stop the bleeding. This simple and fast means for getting a bleed-stopping device into a patient's nose will be very much appreciated by all patients who suffer from this affliction.

Figure 3:
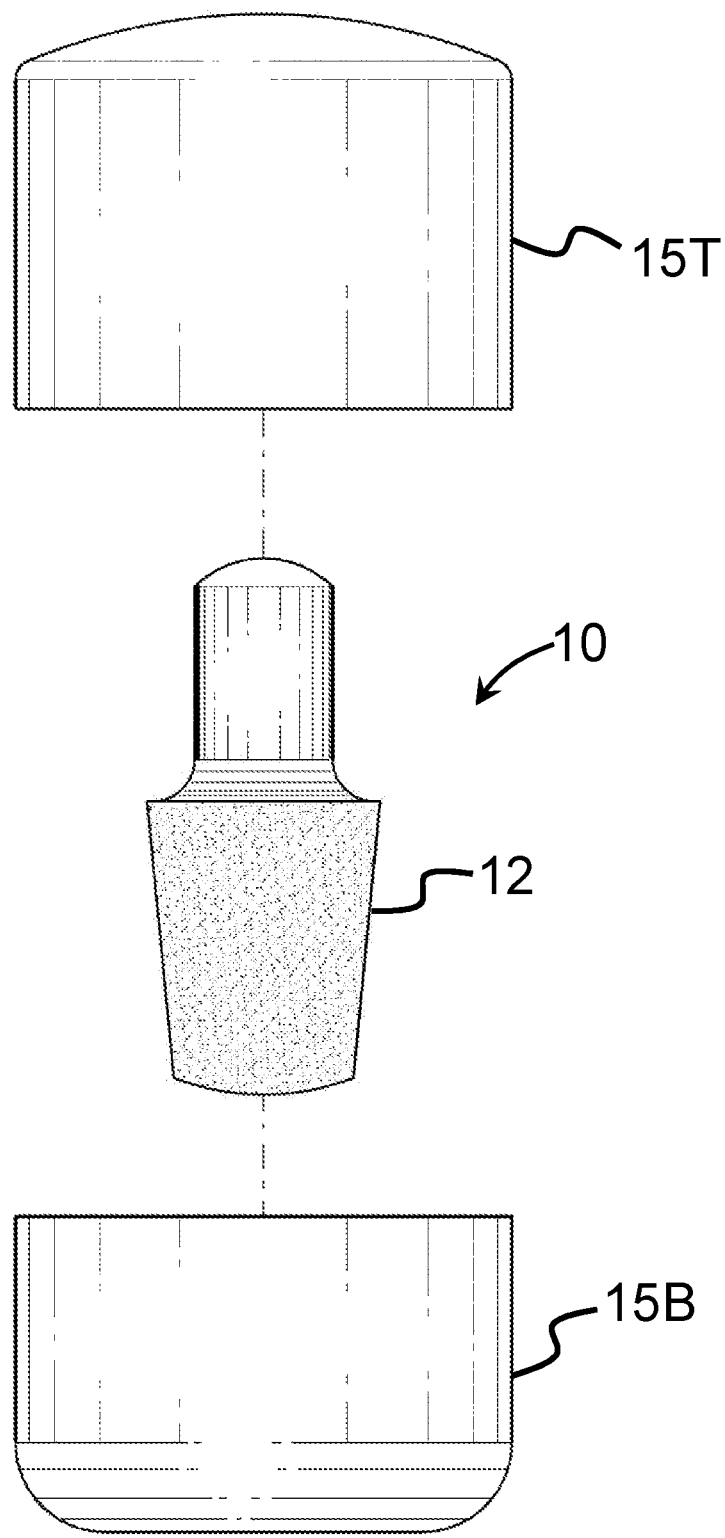
FIG. 3 shows an exterior view of the nose bleed stopping device as shown in FIG. 1 with an outer view of the top piece and bottom piece of the bottle that will contain the nose bleed stopping device prior to its insertion into a patient's nostril.

FIG. 3 shows an exterior view of the device 10 for stopping nose bleeds before it is inserted into the bottom section 15B of the bottle 15 before the bottle top section 15T is screwed (or slid) into the bottom section 15B so as to securely contain the device 10.

Although FIGS. 2 and 3 illustrate a specific (and ideal) shape for a container 15 for the device 10, it should be understood that other shapes for containers could be used to hold the device 10 and that would still be within the scope of this invention. For example, a small plastic bag (not shown) or a small box (not shown) could also be used for containing the device for insertion into the patient's nostril to stop a nose bleed.

Figure 4:
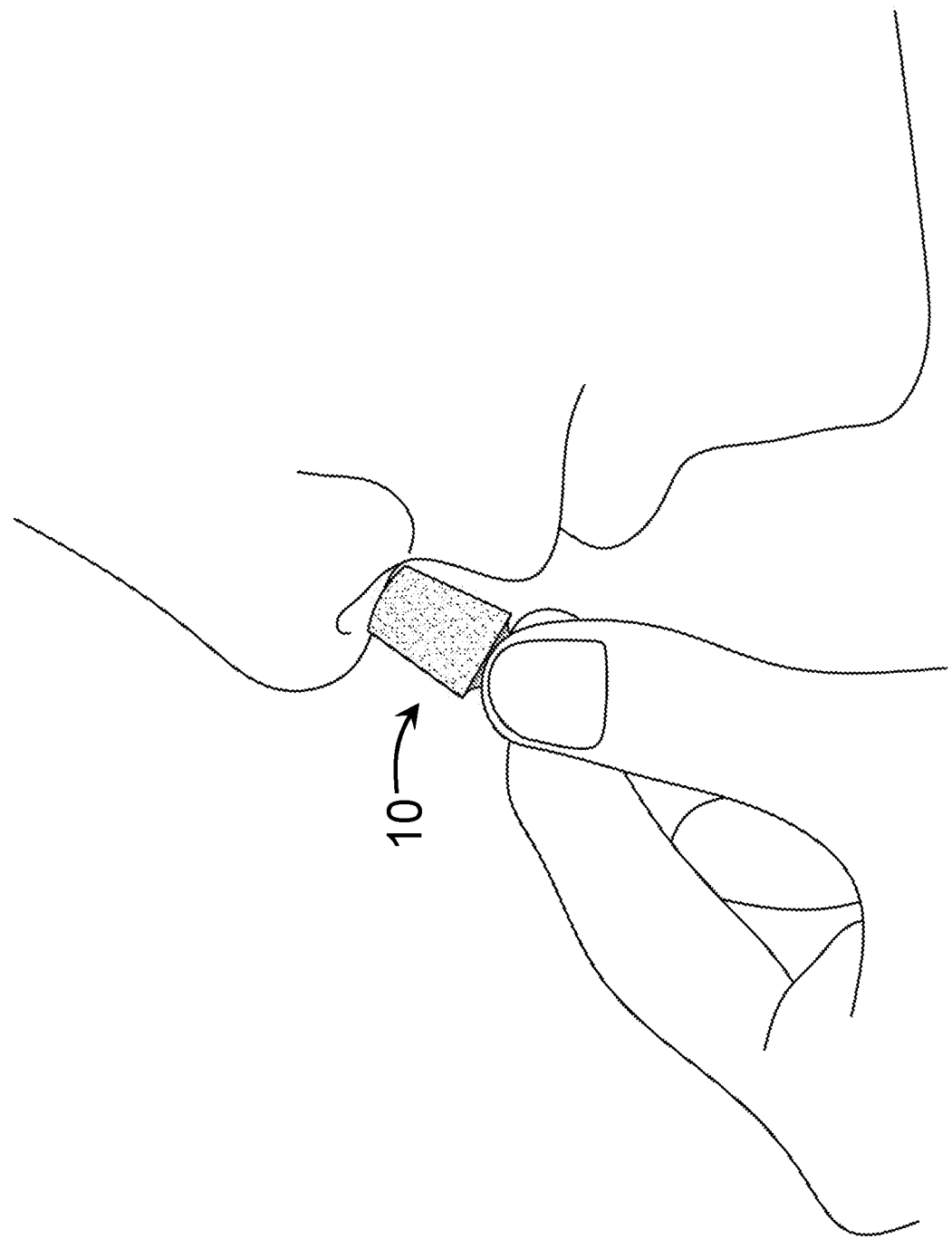
FIG. 4 illustrates the blood clotting device shown in FIG. 1 as it would be inserted into the nose to stop the nose from bleeding.

FIG. 4 illustrates how a patient would hold the device 10 for placement into that patient's nose to stop the bleeding from one of that patient's nostrils.

Various other modifications, adaptations and alternative designs are of course possible in light of the teachings as presented herein. Therefore, it should be understood that while still remaining within the scope and meaning of the appended claims, this invention could be practiced in a manner other than that which is specifically described herein.

What is claimed is:

1. A system to stop bleeding from inside the nostril of a human patient's nose, the system including:
    a device having a distal end, a proximal end, and a middle flange-like section between said distal and proximal ends, said device being configured with an upper sponge-like portion extending between said distal end and middle flange-like section, wherein said upper sponge-like portion has a size and a shape adapted for insertion into a patient's nose, the upper sponge-like portion including a rigid interior portion extending longitudinally of said device to form a rigid handle extending coaxially with said upper sponge-like portion between said middle flange-like section and proximal end of said device and configured for insertion into and removal from a patient's nose, the outer surface of the upper sponge-like portion being coated with a drug capable of assisting in stopping nose bleeding, and a bottle configured with a bottom section and an upper section removably secured to said bottom section, said bottom section of said bottle being configured to receive and hold therein the upper sponge-like portion of the device, and said upper section of the bottle being configured to receive therein the rigid handle of said device, wherein said device is configured with a channel extending longitudinally between said distal and proximal ends of said device along said rigid interior portion and rigid handle, said channel terminating in an opening at said proximal end of said device to pass blood from inside of a patient's nose to expel to an outside of said device through an said opening formed at the proximal end of said device, wherein the channel is configured to transport liquids without absorbing or obstructing the flow liquids.

2. The device of claim 1 wherein said upper sponge-like portion is formed with said sponge-like tapered surface impregnated with said drug, said drug having a capability to clot blood and to stop nose bleeding, said drug including a drug selected from a group including chitosan, aluminum chloride-6-hydrate 21.3%, and combinations thereof.

3. The device of claim 2 wherein at least 70% of the tapered upper sponge-like portion of the device is housed within the bottom section of the bottle.

4. The device of claim 1 wherein said bottle is fabricated from a hard or firm plastic.

5. The device of claim 1 wherein said middle flange-like section of said device is configured with a flange connecting said upper portion and handle of said device, wherein said upper portion of the device has a tapered configuration with a diameter of said upper portion at said distal end thereof being smaller than a diameter of said flange and larger than a diameter of the handle.

6. The device of claim 1 wherein said channel extends through the entire length of the device.

7. A method for the treatment of a bleeding nostril of a human nose, the method consisting of:

a) configuring a device with a sponge-like material forming a tapered upper portion in proximity to a distal end of said device and a substantially cylindrical rigid plastic handle in proximity to a proximal end of said device, said rigid plastic handle being integrally connected with said tapered upper portion and extending co-axially therewith, wherein an outer surface of the tapered upper portion is coated with a material capable of blood clotting, and wherein said device is formed with a channel extending longitudinally inside of said tapered upper portion and said rigid plastic handle, and terminating in an opening at said proximal end of said device, wherein the channel is configured to transport liquids without absorbing or obstructing the flow liquids;

b) configuring a bottle for housing said device, said bottle having a bottom section and an upper section removably attached to said bottom section, said device being housed within said bottle, wherein said bottom section has an interior contoured to secure the tapered upper portion of the device therein, and wherein, when the upper section of the bottle is removed from said bottom section, the rigid handle of the device is accessible for removal of said device from said bottom section of said bottle for insertion of said device into a nose;

c) unscrewing the upper section of the bottle from the bottom section of the bottle and removing the device to be inserted into a nose by holding the bottom section of the bottle with a user's fingers of one hand and pulling outward the rigid handle of the device to be inserted into a patient's nostril with a user's fingers of another hand;

d) holding the rigid handle of the device for insertion into the nose with a user's thumb and one other finger;

e) inserting the device into the nostril of a human nose where the bleeding originates and expelling blood to outside of the device from the human nose through said opening of said channel; and f) pulling downward on the rigid handle to remove the device from a patient's nostril after the bleeding has been stopped.

8. The method of claim 7 wherein the material causing the blood to clot includes chitosan, aluminum chloride-6-hydride 21.3%, and combinations thereof.

9. A blood coagulant device assembly comprising:

a) a blood coagulant device configured for insertion into a nostril of a patient, said blood coagulant device being formed with a channel extending longitudinally inside of said blood coagulant device and terminating in an opening at a proximal end of said blood coagulant device, wherein the channel is configured to transport liquids without absorbing or obstructing the flow liquids; and b) a blood coagulant device container having a container upper section and a container bottom section secured to and releasable each from the other for maintaining said blood coagulant device in a fixed position within said blood coagulant device container prior to fully removing said blood coagulant device from the upper and bottom sections of said blood coagulant device container for insertion into a patient's nostril for the treatment of a bleeding nose, wherein blood from the patient's nostril passes through said channel and is expelled from said blood coagulant device externally of said blood coagulant device assembly.

10. The assembly as recited in claim 9 where said blood coagulant device includes:

a handle member having a handle lower section and a handle upper section formed as a one piece formation, said handle lower and upper sections having said channel passing therethrough in an axial direction; and a blood coagulant substance impregnating a sponge-like material secured to an outer surface of said handle's upper section.

11. The assembly as recited in claim 10 where said blood coagulant substance is selected from a group including chitosan, aluminum chloride-6-hydrate 21.3%, and combinations thereof.

12. The assembly as recited in claim 10 where said handle member is formed from a rigid material including a closed cell plastic composition.

13. The assembly as recited in claim 9 where said container upper section and said container lower section, when joined to each other, form a closed container chamber for housing said blood coagulant device therein prior to removal of said blood coagulant device therefrom for insertion into the nose of a patient.

14. The assembly as recited in claim 9 where said container upper section is threadedly secured to said container lower section.

15. The assembly as recited in claim 9 where said container upper section is slideably releasable from said container lower section.

16. The assembly as recited in claim 9 where said container lower section includes a shoulder section for frictionally engaging a side surface of the handle of said blood coagulant device.

17. The assembly as recited in claim 9 where said container lower section includes a lower arcuately contoured internal surface for matingly engaging an arcuately contoured upper surface of said blood coagulant device.

18. The assembly as recited in claim 9 where said container upper section includes an interior upper surface contoured to contact said handle member when said blood coagulant device is mounted in said blood coagulant container.

\* \* \* \* \*